US006252243B1

(12) United States Patent
Isoda et al.

(10) Patent No.: US 6,252,243 B1
(45) Date of Patent: Jun. 26, 2001

(54) STIMULABLE PHOSPHOR SHEET HAVING DIVIDED PHOSPHOR LAYER

(75) Inventors: Yuji Isoda; Kenji Takahashi; Yasuo Iwabuchi; Hiroshi Matsumoto; Katsuhiro Kohda; Seiji Tazaki, all of Ashigara-kami-gun (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/397,926

(22) Filed: Sep. 17, 1999

(30) Foreign Application Priority Data

Sep. 17, 1998 (JP) ... 10-282024
Mar. 15, 1999 (JP) ... 11-068964

(51) Int. Cl.[7] ... A61B 6/00
(52) U.S. Cl. ... 250/581; 250/327.2
(58) Field of Search ... 250/581, 484.4, 250/580, 483.1; 427/64; 430/6, 139

(56) References Cited

U.S. PATENT DOCUMENTS 4,814,619 * 3/1989 Katsuda et al. ... 250/327.2
4,893,012 * 1/1990 Agano et al. ... 250/327.2

* cited by examiner

*Primary Examiner*—Robert H. Kim
*Assistant Examiner*—Pamela R. Hobden
(74) *Attorney, Agent, or Firm*—Sughrue, Mion, Zinn, Macpeak & Seas, PLLC

(57) ABSTRACT

A stimulable phosphor sheet giving a high sensitivity and a high sharpness in a radiation image recording and reproducing method is composed of a partition containing a phosphor that emits a light in a UV or visible region upon absorbing the applied radiation which divides the phosphor sheet on its plane into small sections, and stimulable phosphor-incorporated area which is divided with the partition and which has a reflectivity to stimulating rays differing from a reflectivity to the stimulating rays of the partition.

22 Claims, 13 Drawing Sheets

STIMULABLE PHOSPHOR SHEET HAVING DIVIDED PHOSPHOR LAYER

FIELD OF THE INVENTION

The present invention relates to a stimulable phoshor sheet for the use in the radiation image recording and reproducing method utilizing a stimulable phosphor.

BACKGROUND OF THE INVENTION

As a method replacing a conventional radiography using a combination of a radiographic film and radiographic intensifying screen, a radiation image recording and reproducing method utilizing a stimulable phosphor was proposed and has been practically employed. This recording and reproducing method employs a radiation image storage panel (which is also referred to as "stimulable phosphor sheet") comprising a support and a stimulable phosphor layer provided thereon, and the procedure of the recording and reproducing method comprises the steps of causing the stimulable phosphor of the panel to absorb radiation energy having passed through an object or having radiated from an object; sequentially exciting the stimulable phosphor with an electromagnetic wave such as visible light or infrared rays (hereinafter referred to as "stimulating rays") to release the radiation energy stored in the phosphor as light emission (i.e., stimulated emission); photoelectrically detecting the emitted light for obtaining electric signals; and reproducing the radiation image of the object as a visible image from the electric signals. The panel thus treated is then subjected to a step for erasing a radiation image remaining therein, and then stored for the next recording and reproducing procedure. Thus, the radiation image storage panel can be repeatedly employed.

In general, the above radiation image storage panel (i.e., stimulable phosphor sheet) has a basic structure comprising a support, a stimulable phosphor layer, and a protective film overlaid in order. The stimulable phosphor layer generally comprises a binder and stimulable phosphor particles dispersed therein, but it may consist of agglomerated phosphor with no binder. The phosphor layer containing no binder can be formed by a deposition process or a firing process. Further, a phosphor layer comprising an agglomerated phosphor soaked with a polymer is also known. For the recording and reproducing method, the radiation image storage panels having any types of stimulable phosphor layer are employable.

The radiation image recording and reproducing method is often used in X-ray radiography for medical diagnosis. In that case, it is especially desired to obtain a radiation image of high quality (particularly, high sharpness for high resolution) by applying a relatively small dose of radiation. Therefore, the radiation image storage panel is required to have a high sensitivity and also to provide an image of high quality.

The sharpness of radiation image is mainly affected by diffusion of the stimulating rays in the phosphor layer. In the reproducing process, the procedure for reading the latent image is performed by the steps of sequentially and sweepingly applying a beam of the stimulating rays onto the surface of the phosphor layer to induce the stimulated emission and successively collecting the emission. If the stimulating rays diffuse (horizontally, in particular) in the phosphor layer, they excite the phosphor particles not only at the target spot but also in its periphery area. Consequently, the stimulated emission emitted from the target spot is collected in combination with stimulated emissions emitted from the periphery area. The contamination of the target emission with the emissions from the periphery impairs the sharpness of the resultant radiation image.

For avoiding the diffusion of the stimulating rays, it was proposed to divide the plane of the stimulable phosphor layer into small sections (cells) with a partition which reflects the applied stimulating rays.

Japanese Patent Provisional Publication No. 59-202100 discloses a radiation image storage panel having a honeycomb structure consisting of many small cells filled with stimulable phosphor. The storage panel comprises a substrate and a stimulable phosphor layer provided thereon, and the honey-comb structure sectioned with a partition is further provided on the phosphor layer.

Japanese Patent Provisional Publication No. 62-36599 discloses a storage panel employing a support provided with many hollows regularly arranged on one surface. The hollows are filled with stimulable phosphor, and the ratio of depth to diameter of each hollow is 3.5 or more.

Japanese Patent Provisional Publication No. H5-512636 discloses a process for preparing pixel phosphor with a mold.

Japanese Patent Provisional Publication No. H2-129600 discloses a radiation image storage panel employing a support plate having many holes vertically bored and filled with stimulable phosphor.

Further, Japanese Patent Provisional Publication No. H2-280100 discloses a stimulable phosphor sheet employing a substrate having a honey-comb micro-structure filled with stimulable phosphor.

Japanese Patent Provisional Publication No. H2-176600 describes a stimulable phosphor sheet having a phosphor layer comprising a stimulable phosphor and a phosphor that is excitable by radiation to emit a light in the ultraviolet region, in which the stimulable phosphor absorbs and stores thus emitted ultraviolet light. The sensitivity of the stimulable phosphor panel is increased by the combination of UV light-emitting phosphor and UV light-absorbing stimulable phosphor, because a portion of the applied radiation which is not directly absorbed by the stimulable phosphor but is absorbed by the UV light-emitting phosphor increases the radiation absorption.

In the known radiation image storage panel employing a support or substrate provided with many holes or hollows charged with phosphor, a part of support or substrate serves as a partition keeping the simulating rays from diffusion. Thus prepared radiation image storage panel, therefore, gives a radiation image of high quality (particularly, high sharpness). On the other hand, since the partition of support material partly occupies the phosphor layer in the storage panel, the amount of the phosphor charged in a unit volume of the layer is made relatively small for absorbing an enough amount of X-ray radiation. Consequently, the provision of partition lowers the sensitivity of the storage panel. Although the sensitivity can be enhanced by increasing the thickness of the stimulable phosphor layer, a thick phosphor layer generally impairs the sharpness of the reproduced radiation image.

In X-ray radiography for medical diagnosis, a storage panel or a phosphor sheet of high sensitivity reduces a dose of radiation applied to a patient. Therefore, it is desired to provide a radiation image storage panel or a stimulable phosphor sheet giving an image of high sharpness as well as high sensitivity.

SUMMARY OF THE INVENTION

The present invention resides in a stimulable phosphor sheet for a radiation image recording and reproducing method comprising the steps of recording a radiographic image (which is formed upon application of radiation) as a latent image, irradiating the latent image with stimulating rays to release stimulated emission, and electrically processing the emission to reproduce the radiographic image, which comprises:

a partition containing a phosphor that emits a ultraviolet or visible light upon absorbing the applied radiation, which divides the stimulable phosphor sheet along its plane into small sections, and a stimulable phosphor-incorporated area which is divided with the partition and which has a reflectivity with respect to the stimulating rays differing from a reflectivity with respect to the stimulating rays of the phosphor-containing partition.

In the stimulable phosphor sheet of the invention wherein the reflectivity (or reflectance) of the stimulable phosphor-incorporated area preferably lower (but may be higher) than the reflectivity of the partition. The stimulable phosphor sheet of the invention preferably has a support on one side and a transparent protective film on another side.

In the stimulable phosphor sheet of the invention, the phosphor-containing partition preferably comprises phosphor particles which absorb the applied radiation and emit a UV or visible light and a binder, and the stimulable phosphor-incorporated area preferably comprises stimulable phosphor particles and a binder, and the stimulable phosphor-incorporated area is preferably divided and surrounded with the partition.

The stimulable phosphor sheet of the invention preferably has a stimulating rays-reflecting layer and/or a stimulated emission-reflecting layer on a surface opposite to the surface on which the stimulating rays impinge.

In the stimulable phosphor sheet of the invention, the UV or visible light-emitting phosphor-containing partition preferably has a height in the range of 1/3 to 1/1 of the thickness of the stimulable phosphor sheet, and preferably contains white fine particles (pigment) and/or a dye absorbing the stimulating rays. The stimulable phosphor-incorporated area preferably contains a dye which absorbs the stimulating rays.

In the stimulable phosphor sheet of the invention, it is preferred that the UV or visible light-emitting phosphor contained in the partition and the stimulable phosphor incorporated in the stimulable phosphor-incorporated area both are in the form of fine particles, and the phosphor in the partition has a mean particle size smaller than that of the stimulable phosphor in the stimulable phosphor-incorporated area. Otherwise, the UV or visible light-emitting phosphor contained in the partition and the stimulable phosphor incorporated in the stimulable phosphor-incorporated area both are in the form of fine particles, and the phosphor in the partition has a mean particle size larger than that of the stimulable phosphor in the stimulable phosphor-incorporated area.

In the stimulable phosphor sheet of the invention, the phosphor-containing partition preferably comprises UV or visible light-emitting phosphors and a binder, and the stimulable phosphor-incorporated area preferably comprises stimulable phosphor particles and a binder, and a weight ratio of the phosphor particles to the binder in the partition is larger or smaller than a weight ratio of the phosphor particles to the binder in the stimulable phosphor-incorporated area.

The invention further resides in a radiation image recording and reproducing method which comprises the steps of:

recording a radiographic image on the stimulable phosphor sheet of the invention as a latent image, irradiating the latent image with stimulating rays to release stimulated emission, and electrically processing the stimulated emission to reproduce the recorded radiographic image.

The invention further resides in a radiation image recording and reproducing method which comprises the steps of:

recording a radiographic image on the stimulable phosphor sheet of the invention as a latent image, irradiating the latent image with stimulating rays to release stimulated emission, collecting the stimulated emission from both surfaces of the stimulable phosphor sheet, and electrically processing the collected emissions to reproduce the recorded radiographic image.

The invention furthermore resides in a radiation image recording and reproducing method which comprises the steps of:

recording a radiographic image on the stimulable phosphor sheet of the invention as a latent image, irradiating the latent image with stimulating rays transmitted through a guide to release stimulated emission, under the condition that the stimulating rays are applied simultaneously in line in a direction traversing the stimulable phosphor sheet which moves in one direction relative to the position of the stimulating rays-transmitting guide, collecting the stimulated emission simultaneously on the line on which the stimulating rays are applied, and electrically processing the collected emission to reproduce the recorded radiographic image.

In the last described radiation image recording and reproducing method, it is preferred to employ a stimulable phosphor sheet which has, on a surface to be irradiated with the stimulating rays, a multi-layer filter having a reflectivity with respect to the stimulating rays which increases as an angle at which the stimulating rays are applied to the stimulable phosphor sheet increases and a reflectivity with respect to the stimulated emission which does not vary as an angle at which the stimulated emission comes out varies.

Also preferred is that the stimulating rays comprises fluorescence and the guide is a sheet comprising phosphor particles and a polymer binder which receives a light on one end or on one surface and then emits fluorescence from another end for irradiating the stimulable phosphor sheet simultaneously in line. In this method, the stimulated emission emitted in line is preferably collected simultaneously by a line sensor comprising plural solid photoelectric conversion elements aligned in one direction.

DETAILED DESCRIPTION OF THE INVENTION

Figure 1:
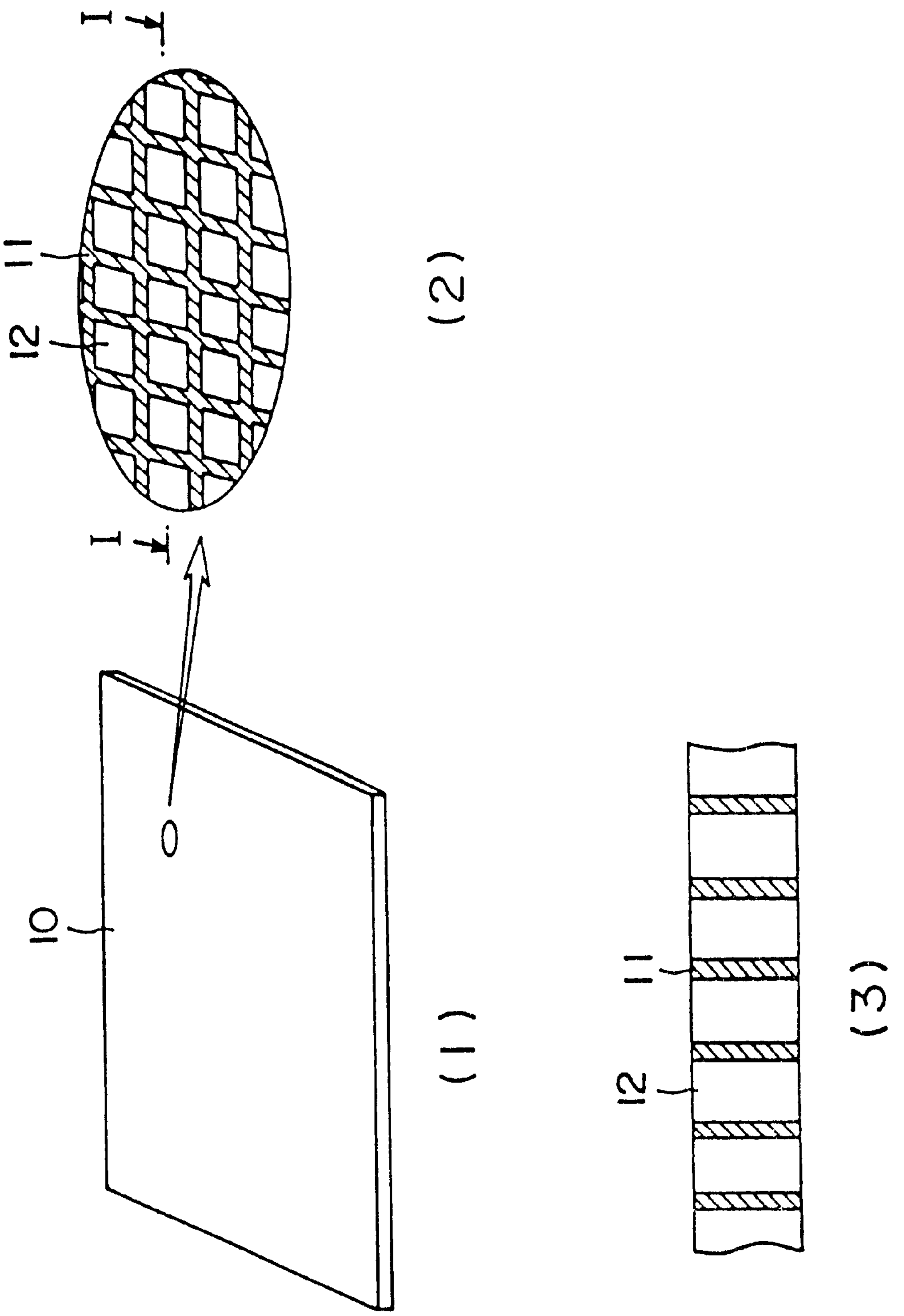
FIGS. 1-(1), -(2) and -(3) are a sketch showing a stimulable phosphor sheet of the invention, a partial enlarged drawing of (1) and a partial sectional view of (2) sectioned with I—I line, respectively.

The stimulable phosphor sheet of the invention can be used in the known radiation image recording and reproducing method, and is characterized by providing a partition which comprises a phosphor that absorbs radiation and emits a UV or visible light (which generally means a light in the wavelength region of 200 to 700 nm, preferably a spontaneous emission in the UV region). The partition divides the plane of the phosphor sheet into small sections. The stimulable phosphor-incorporated area which is divided with the partition has characteristics different from those of the partition in reflecting the stimulating rays. Since the partition of the stimulable phosphor sheet of the invention contains a phosphor which emits UV or visible light upon absorbing the applied radiation, and the emitted UV or visible light is then absorbed by the stimulable phosphor placed in the adjacent area, it can keep, without lowering the sensitivity, the stimulating rays from diffusing horizontally in the stimulable phosphor sheet. Consequently, the stimulable phosphor sheet of the invention gives an image of high sharpness at high sensitivity.

From the viewpoint of fundamental performance, it is not necessary for the stimulable phosphor sheet of the invention to have a protective film and a support. Nevertheless, the stimulable phosphor sheet is preferably provided with a transparent protective film and a support for ensuring safety of transportation and for avoiding deterioration, and hence a typical embodiment of the sheet comprises a relatively thick support and a relatively thin transparent protective film provided on the bottom and on the top surface, respectively. By taking an example of the stimulable phosphor sheet having the above-described structure (which is often referred to as "radiation image storage panel"), the present invention is described below. In the following, a stimulable phosphor sheet in the storage panel structure is often referred to as "stimulable phosphor layer" or simply "phosphor layer".

As the support of the radiation image storage panel, a sheet or a film of flexible resin material having a thickness of 50 $\mu$m to 1 mm is generally employed. The support may be transparent or may contain light-reflecting material (e.g., titanium dioxide particles, barium sulfate particles) or voids for reflecting the stimulating rays or the stimulated emission. Further, it may contain light-absorbing material (e.g., carbon black) for absorbing the stimulating rays or the stimulated emission. Examples of the resin materials include polyethylene terephthalate, polyethylene naphthalate, aromatic polyamide resin, and polyimide resin. The support may be a sheet of other material such as metal, ceramic, or glass, if required. On the phosphor layer-side surface of the support, any auxiliary layers (e.g., light-reflecting layer, light-absorbing layer, adhesive layer, and electroconductive layer) may be placed or many small hollows may be provided. On the other side surface, a friction-reducing layer or an anti-scratch layer may be placed.

The stimulable phosphor layer (stimulable phosphor sheet) is provided on the support. The phosphor layer according to the invention comprises a partition which contains a UV or visible light-emitting phosphor and divides the plane of the layer into small sections, and a stimulable phosphor-incorporated area which is divided with the UV or visible light-emitting phosphor-containing partition and which has characteristics different from those of the partition in reflecting the stimulating rays. By referring to the attached drawings, the structures of the stimulable phosphor layer (or stimulable phosphor sheet) are described in more detail.

FIG. 1-(1) is a sketch showing a stimulable phosphor sheet 10 of the invention. FIG. 1-(2) is a partial enlarged view of FIG. 1-(1). FIG. 1-(3) is a partial sectional view of FIG. 1-(2) along I—I line. The shadowed portions in FIG. 1-(2) and FIG. 1-(3) indicate the UV or visible light-emitting phosphor-containing partition 11, and the part divided with the shadowed portion is the stimulable phosphor-incorporated area 12. The thickness of the stimulable phosphor layer (or stimulable phosphor sheet) generally is in the range of 20 $\mu$m to 1 mm, preferably 50 $\mu$m to 500 $\mu$m. Preferably, the partition has a width or thickness of 5 $\mu$m to 50 $\mu$m, and each divided area (cell) of the stimulable phosphor-incorporated area 12 has a width of 20 $\mu$m to 200 $\mu$m on average.

Figure 2:
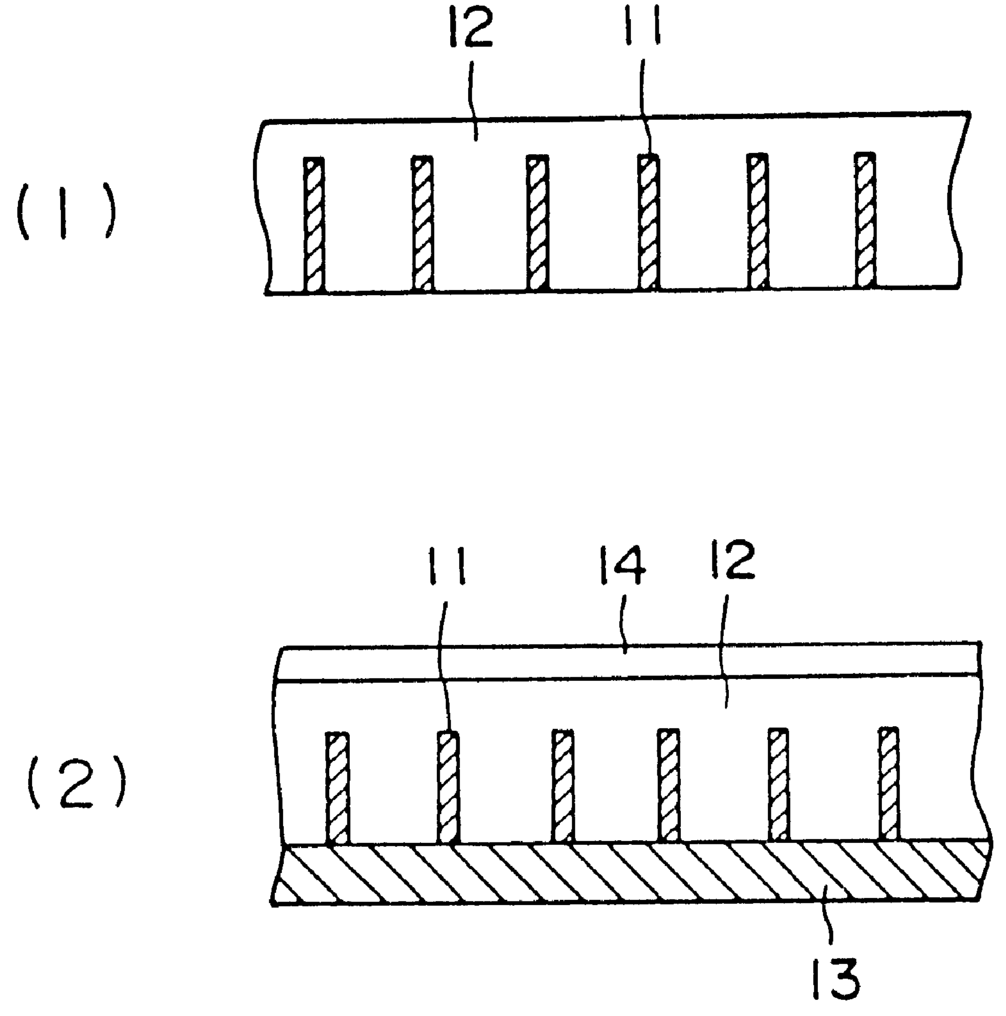
FIG. 2-(1) shows a sectional view of another embodiment of the invention, and FIG. 2-(2) is a sectional view of the sheet of FIG. 2-(1) provided with a protective film and a support on the top and the bottom surfaces, respectively.

The top and the bottom of the partition in FIG. 1 appear on the surfaces of the layer, but both or one of them may be buried in the layer. Preferably, the height of the partition is in the range of 1/3 to 1/1 of the thickness of the phosphor layer. FIG. 2-(1) shows another stimulable phosphor sheet of the invention in which the top of the partition is buried in the layer. FIG. 2-(2) is a sectional view of the stimulable phosphor sheet of FIG. 2-(1) provided with a support 13 and a protective film 14 on the bottom and the top surfaces, respectively.

Figure 3:
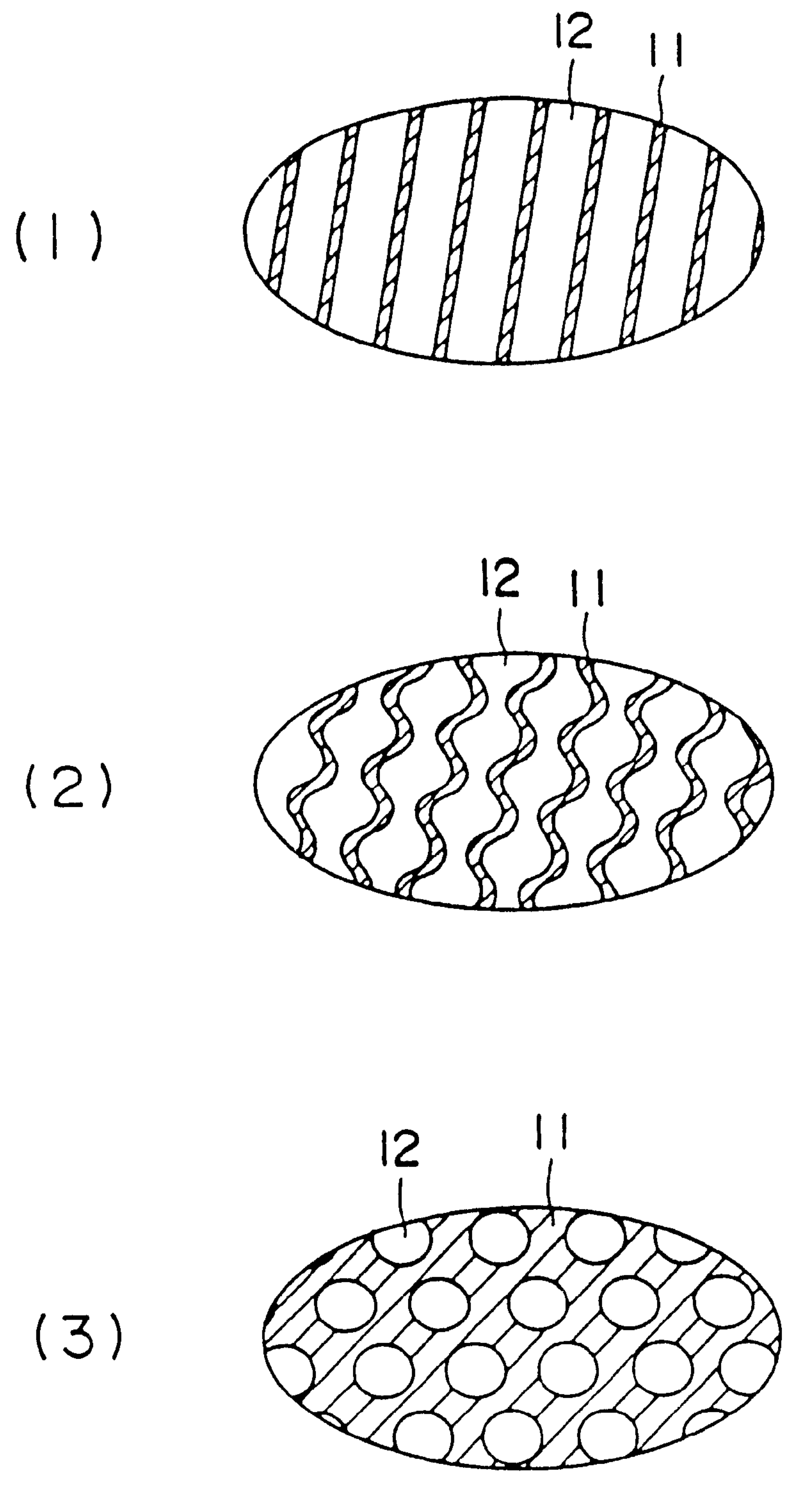
FIGS. 3-(1), -(2) and -(3) are sketches schematically showing combination patterns of the UV or visible light-emitting phosphor-containing partition and the stimulable phosphor-incorporated area.

The plane of the stimulable phosphor sheet shown in FIG. 1 is divided with the latticed partition 11, and each pseudo-rectangular area (cell) formed with the partition 11 is filled with stimulable phosphor. However, the design and the position of the partition can be changed, if desired. FIG. 3 shows some examples of designs or arrangement of the UV or visible light-emitting phosphor-containing partition. In the sheet of FIG. 3-(1), the straight lines of the partition 11 divide the phosphor layer in the form of strips, and each strip of the area 12 sectioned with the partition 11 is filled with stimulable phosphor. In reading a radiation image stored in the sheet of FIG. 3-(1), it is preferred to scan a beam of the stimulating rays in the direction crossing or traversing the partition 11 and the striped area 12.

FIG. 3-(2) indicates another pattern or arrangement of the partition. In the stimulable phosphor sheet of FIG. 3-(2), the waved lines of the partition 11 divide the plane of the phosphor layer, and each waved strip of the area 12 divided with the partition 11 is filled with stimulable phosphor. In reading an image stored in the stimulable phosphor sheet of FIG. 3-(2), it is also preferred to scan a beam of the stimulating rays in the direction crossing or traversing the waved partition 11 and the striped area 12.

The stimulable phosphor sheet shown in FIG. 3-(3) comprises columns of the stimulable phosphor-incorporated area 12 surrounded with the UV or visible light-emitting phosphor-containing partition 11.

As the stimulable phosphor to be incorporated in the phosphor-incorporated area, a phosphor which absorbs not only a radiation having a wavelength of lower than 250 nm but also a visible or ultraviolet light in the wavelength region of 250 to 400 nm, and gives a stimulated emission of a wavelength in the range of 300 to 500 nm when it is irradiated with stimulating rays of a wavelength in the range of 400 to 900 nm is preferably employed. In Japanese Patent Provisional Publications No. H2-193100 and No. H4-310900, some preferred examples of such stimulable phosphors are described in detail. Examples of the preferred stimulable phosphors include divalent europium activated or cerium activated alkaline earth metal halide phosphors (e.g., BaFBr:Eu, BaFBrI:Eu), and cerium activated oxyhalide phosphors. Also preferably employable is a phosphor having the formula of $YLuSiO_5$:Ce,Zr. These and other stimulable phosphor which absorb a ultraviolet or visible light are described in detail in the aforementioned Japanese Patent Provisional Publication No. H2-176600.

The UV or visible light-emitting phosphor to be incorporated in the partition emits a light having a emission peak wavelength in the ultraviolet or visible region. A phosphor emitting a ultraviolet light is preferred. Specifically preferred is a phosphor which absorbs a radiation having a wavelength of lower than 250 nm and emits a spontaneous emission in the ultraviolet region (i.e., wavelength range of 250 to 400 nm). Examples of the preferred UV or visible light-emitting phosphors include $YTaO_4$, $YTaO_4$:Gd, LnOX:Ac (in which Ln is Y, La, Ga and/or Lu, X is Cl, Br and/or I, and Ac is Bi and/or Gd), $LnF_3$:Ce (in which Ln is Y, La, Ga and/or Lu), $GdF_3$, and $BaF_2$. Also employed are ultraviolet light-emitting phosphors described in the aforementioned Japanese Patent Provisional Publication No. H2-176600.

The UV or visible light-emitting phosphor particles and a binder are well mixed in an appropriate solvent to give a coating dispersion for preparing the partition. Likewise, the stimulable phosphor particles and a binder are well mixed in an appropriate solvent to give a coating dispersion for preparing the stimulable phosphor layer. In both coating dispersions, the binder and the phosphor particles are introduced generally at a ratio of 1:1 to 1:100 (binder:phosphor, by weight), preferably 1:8 to 1:40 (by weight). As the binder material, various known resins are employable.

The stimulable phosphor sheet of the invention comprises a UV or visible light-emitting phosphor-containing partition which divides the plane of the sheet into small sections, and a stimulable phosphor-incorporated area which is divided with the partition. The stimulable phosphor-incorporated area (cell) has a reflectivity differing that of the UV or visible light-emitting phosphor-containing partition. The reflectivity is determined using the stimulating rays to be employed in the radiation image recording and reproducing method.

The preferred embodiments of the invention include:

1) the stimulable phosphor sheet in which the phosphor-incorporated area reflects the stimulating rays at a reflectivity or reflectance lower than that of the partition; and 2) the stimulable phosphor sheet in which the phosphor-incorporated area reflects the stimulating rays at a reflectivity or reflectance higher than that of the partition.

From the viewpoint of the sharpness, the stimulable phosphor sheet of 1) is preferred. The partition or the phosphor-incorporated area can be made to more reflect the stimulating rays by various methods. For example, the reflectivity can be increased by increasing the weight ratio of phosphor/binder, by using smaller phosphor particles or by incorporating light-reflecting particles such as white pigments (e.g., titanium dioxide particles, barium sulfate particles, and alumina particles) and non-stimulable phosphor particles (which exhibit no stimulated emission). Those methods can be used singly or in combination. Further or otherwise, a light-reflecting film may be provided on the interface between the partition and the phosphor-incorporated area.

In contrast, it is also possible to make the partition or the phosphor-incorporated area less reflecting the stimulating rays by various methods. For example, the reflectivity can be decreased by decreasing the weight ratio of phosphor/binder, by using larger phosphor particles or by incorporating a light-absorbing dye. Those methods can be used singly or in combination. Further or otherwise, a light-absorbing film may be provided on the interface between the partition and the phosphor-incorporated area.

The stimulable phosphor sheet of the invention can be produced, for example, by the steps of beforehand preparing a UV or visible light-emitting phosphor-containing sheet having a honey-comb structure comprising many hollows or holes, filling the hollows or holes with a dispersion containing stimulable phosphor particles dispersed in a binder, and then drying the applied dispersion. After filling with the stimulable phosphor, the hollows or holes may be subjected to firing process. Further, it is also possible to charge the hollows or holes with the stimulable phosphor through deposition process.

The stimulable phosphor sheet of the invention can be also produced in the following manner. First, the UV or visible light-emitting phosphor is molded or mixed with a thermosetting resin to form a lump having honeycomb structure. The honey-comb lump of the phosphor thus formed is then pushed into a plastic stimulable phosphor sheet beforehand prepared. In the course of pushing the lump, the sheet may be heated and/or pressed.

The stimulable phosphor sheet having a honey-comb structure can be also formed, for example, by etching process with lithography (dry-etching treatment). Japanese Patent Provisional Publication No. 62-36599 describes s dry-etching treatment employable for the preparation of the stimulable sheet of the invention. Further, LIGA process and etching process with a laser (e.g., excimer laser) are also employable.

The stimulable phosphor sheet of the invention having the divided phosphor layer can be prepared from plural stimulable phosphor films and plural UV or visible light-emitting phosphor films having reflectivity differing from the former stimulable phosphor films by laminating and slicing process which are illustrated on FIGS. 4 to 10 in the attached drawings. The details of the laminating and slicing process are described by referring to FIG. 4 to FIG. 10.

Figure 4:
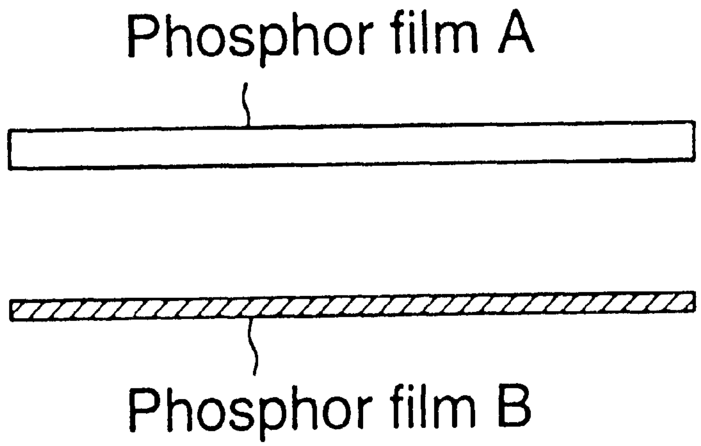
FIG. 4 illustrates two stimulable phosphor films A, B which are employed in a laminating-slicing process for preparing a stimulable phosphor sheet having a divided stimulable phosphor layer.
Figure 5:
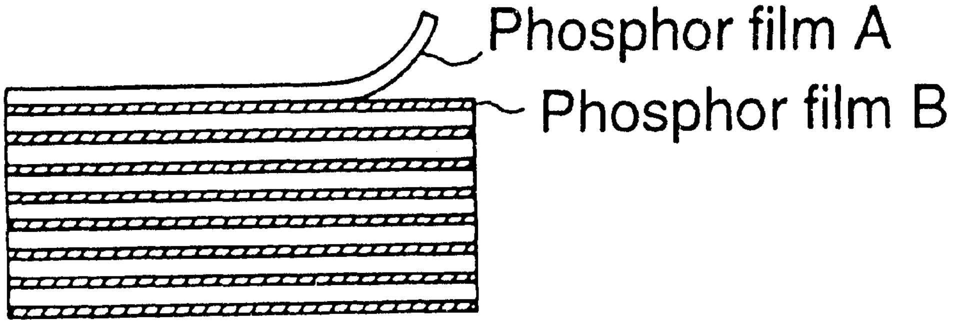
FIG. 5 illustrates a step for preparing a laminate using the phosphor film A (which is to form a stimulable phosphor-incorporated area) and the phosphor film B (which is to form a UV or visible light-emitting phosphor-containing partition).

As illustrated in FIGS. 4 and 5, a plurality of phosphor films (A) comprising stimulable phosphor particles and binder (which form the stimulable phosphor-incorporated area) and a plurality of phosphor films (B) comprising UV or visible light-emitting phosphor particles and binder (which form the UV or visible light-emitting phosphor-containing partition) are independently prepared. The phosphor films A and the phosphor films B are placed alternately one on another to produce a laminate, as illustrated in FIG. 5. Thus produced laminate is heated under pressure, as illustrated in FIG. 6, to give a laminate block in which adjoining phosphor films are combined tightly with each other.

Figure 6:
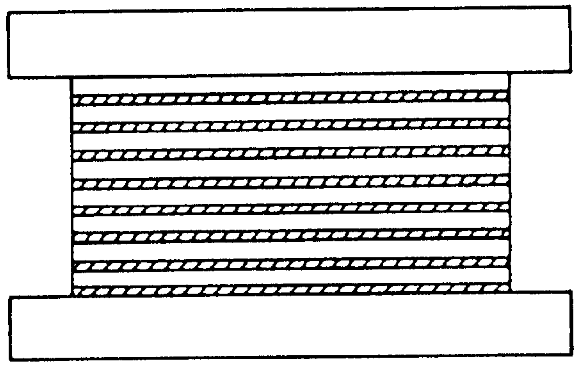
FIG. 6 illustrates a step for preparing a laminate block from the laminate of FIG. 5.
Figure 7:
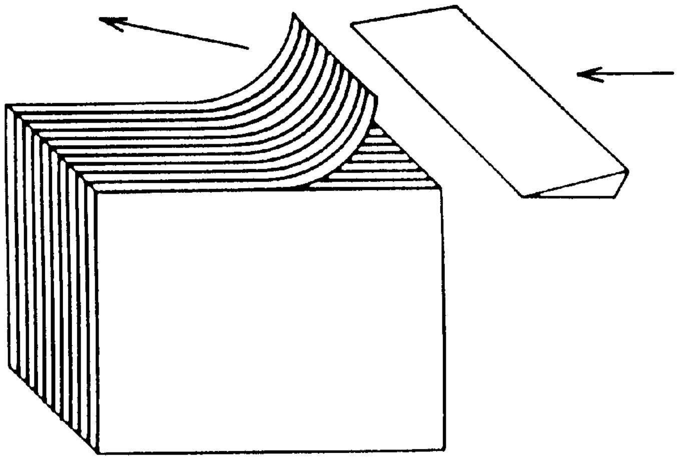
FIG. 7 illustrates a step for preparing a striped phosphor film by slicing the laminate block of FIG. 6.
Figure 8:
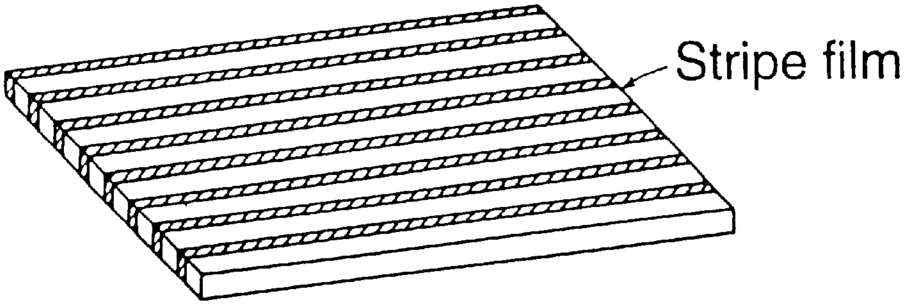
FIG. 8 illustrates a striped phosphor film prepared in the step of FIG. 7.

Subsequently, the laminate block of FIG. 6 is sliced along the plane on which the side ends of the phosphor film (A) and the phosphor film (B) appear, as illustrated in FIG. 7, to give a plurality of striped phosphor films of FIG. 8, in which stripes of the phosphor film (A) and stripes of the phosphor film (B) are alternately positioned in parallel.

Figure 9:
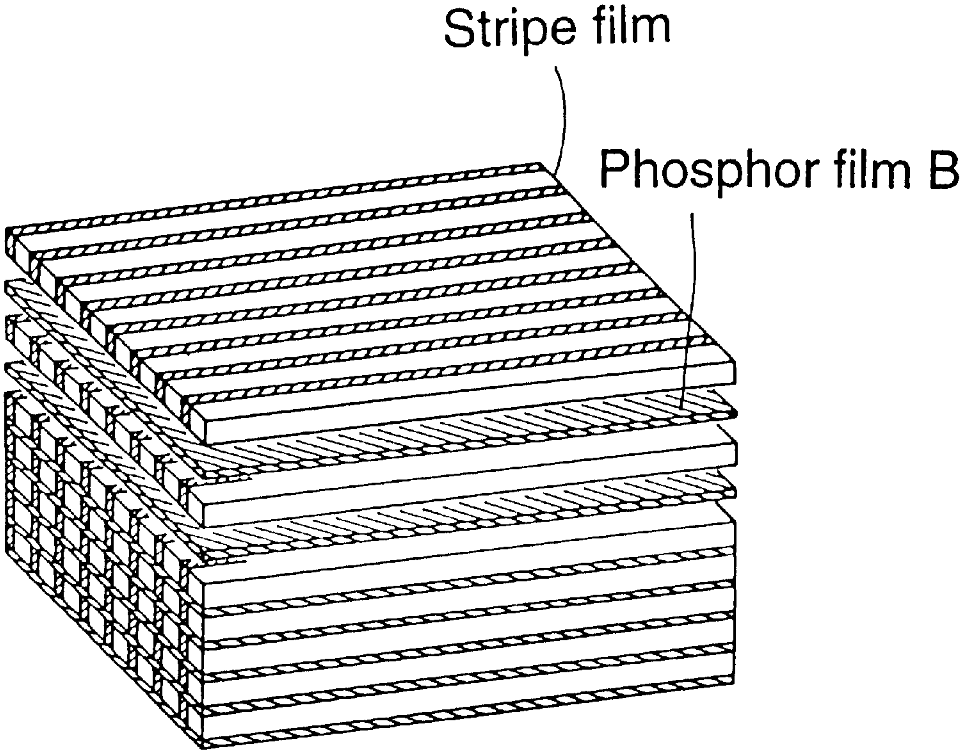
FIG. 9 illustrates a step for preparing-a laminate using the striped phosphor film of FIG. 8 and the phosphor film B (which is to form a stimulable phosphor-containing partition).
Figure 10:
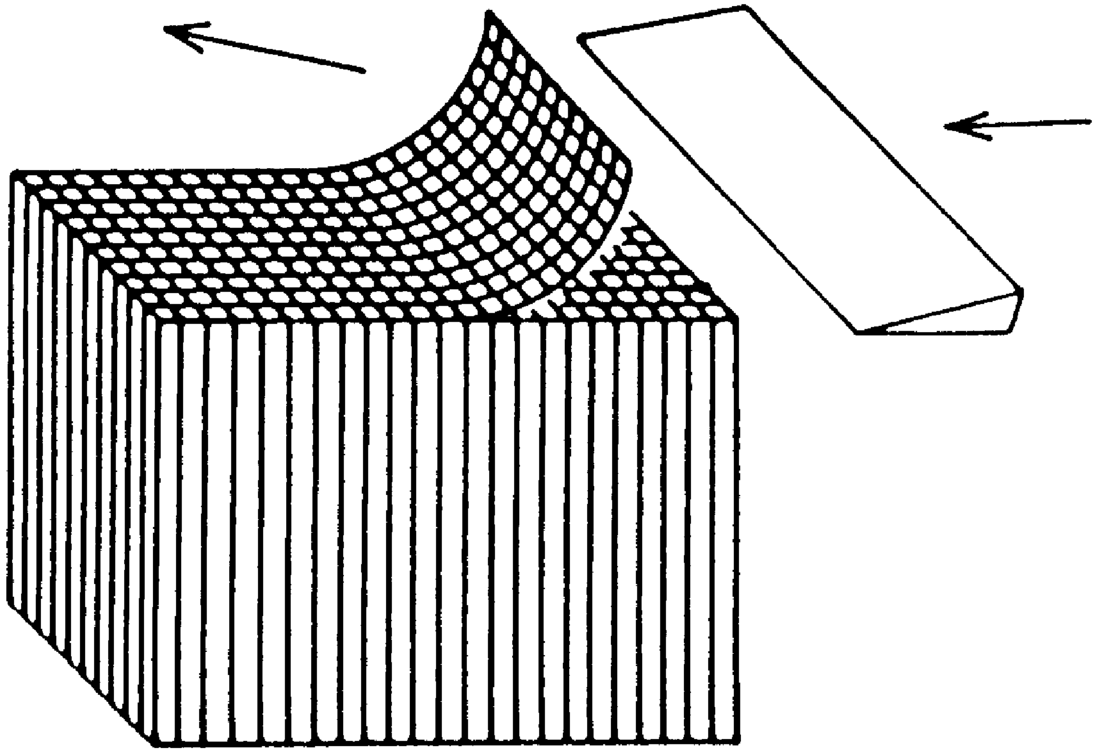
FIG. 10 illustrates a step for preparing the stimulable phosphor sheet having the divided phosphor layer from the laminate of FIG. 9.

The plural striped phosphor films and the phosphor films (B) are then placed alternately one on another, as illustrated in FIG. 9, to produce a laminate in the form of that illustrated in FIG. 5, which is then heated under pressure in the manner as illustrated in FIG. 6 to produced a laminate block. The laminate block is sliced in the manner as illustrated in FIG. 10 to give the desired stimulable phosphor sheet having divided stimulable phosphor layer.

On one surface of the stimulable phosphor sheet of the invention, a layer for reflecting the stimulating rays or the stimulated emission is preferably provided. This light-reflecting layer enhances the sensitivity of the sheet. The light-reflecting layer may comprise white pigments (e.g., titanium dioxide particles, barium sulfate particles, or alumina particles) or non-stimulable phosphor particles (which exhibit no stimulated emission) dispersed in a binder. Since the stimulable phosphor sheet of the invention is preferably provided on a support, the light-reflecting layer is generally arranged between the phosphor sheet and the support. In place of the light-reflecting layer, a light-absorbing layer may be provided between them to improve the sharpness.

On the surface not facing the support, the phosphor sheet preferably has a protective film. In order not to affect the simulating rays or the stimulated emission, the protective film preferably is transparent. For protecting the stimulable phosphor sheet from chemical deterioration and physical shock, it is preferred that the protective film is both chemically stable and physically strong.

The protective film can be provided by fixing a beforehand prepared plastic film on the phosphor sheet with adhesive, or by coating the phosphor sheet with a solution of protective film material and drying the coated solution. Into the protective film, a fine particle filler may be incorporated so as to reduce blotches caused by interference and to improve the quality of the resultant radiation image. Examples of preferred materials for the preparation of the transparent plastic film include polyester resins (e.g., polyethylene terephthalate and polyethylene naphthalate), cellulose derivatives (e.g., cellulose triacetate), and other various resin materials such as polyolefin and polyamide. The thickness of the protective film generally is in the range of not more than 30 $\mu$m, preferably in the range of 1 to 15 $\mu$m, more preferably 5 to 12 $\mu$m.

For enhancing the resistance to stain, a fluororesin layer is preferably provided on the protective film. The fluororesin layer can be formed by coating the surface of the protective film with a solution containing a fluororesin in an organic solvent, and drying the coated solution. The fluororesin may be used singly, but a mixture of the fluororesin and a film-forming resin is preferably employed. In the mixture, an oligomer having a polysiloxane structure or perfluoroalkyl group can be further added. The coating can be performed using known coating means such as a doctor blade, a roll coater, and a knife coater. In the fluororesin layer, a fine particle filler may be incorporated so as to reduce blotches caused by interference and to improve the quality of the resultant radiation image. The thickness of the fluororesin layer generally is in the range of 0.5 to 20 $\mu$m, preferably 1 to 5 $\mu$m. In the formation of the fluororesin layer, additives such as crosslinking agents, film-hardening agents and anti-yellowing agents can be used. In particular, the crosslinking agent is advantageously used to improve durability of the fluororesin layer.

The stimulable phosphor sheet of the invention can be employed in the known radiation image recording and reproducing method which comprises the steps of:

recording a radiographic image on the stimulable phosphor sheet as a latent image, irradiating the latent image with stimulating rays to release stimulated emission, and electrically processing the stimulated emission to reproduce the recorded radiographic image.

In the radiation image reproducing step of the radiation image recording and reproducing method employing the stimulable phosphor sheet of the invention, the stimulated emission can be collected from one surface side of the phosphor sheet or from both surface sides of the phosphor sheet. The latter system, which is named "double-side reading system", is preferably employed in combination with the stimulable phosphor sheet of the invention.

In more detail, the double-side reading system comprises the steps of:

recording a radiographic image on the stimulable phosphor sheet as a latent image, irradiating the latent image with stimulating rays to release stimulated emission, collecting the stimulated emission from both surfaces of the stimulable phosphor sheet, and electrically processing the collected emissions to reproduce the recorded radiographic image.

The double-side reading system is further described with reference to the attached FIG. 11.

Figure 11:
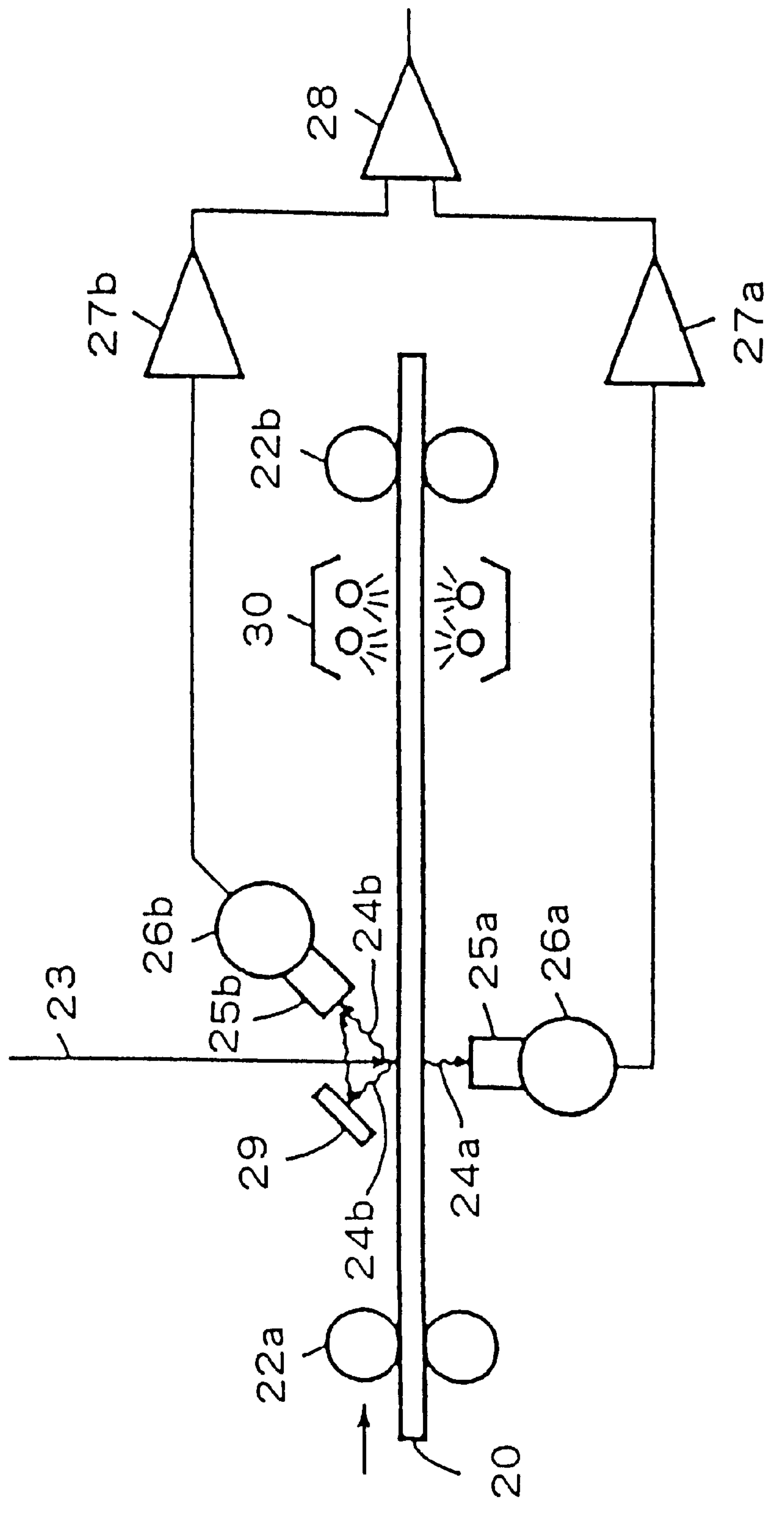
FIG. 11 is a schematic view illustrating a radiation image reproducing device for the use in the double-side reading system.

In FIG. 11, the radiation image storage panel 20 is transferred (or moved) by a combination of two sets of nip rolls *22a, 22b*. The stimulating rays such as laser beam 23 is applied to the storage panel 20 on one side, and the light emitted by the phosphor particles advances upward and downward (in other words, toward both the upper and lower surfaces). The downward light *24a* is collected by a light collector *25a* (arranged on the lower side), converted into an electric signal in a photoelectric conversion device (e.g., photomultiplier) *26a,* multiplied in a multiplier *27a,* and then sent to a signal processor 28. On the other hand, the upward light *24b* is directly, or after reflection on a mirror 29, collected by a light collector *25b* (arranged on the upper side), converted into an electric signal in a photoelectric conversion device (e.g., photomultiplier) 26*b*, multiplied in a multiplier 27*b*, and then sent to the signal processor 28. In the signal processor 28, the electric signals sent from the multipliers 27*a*, 27*b* are processed in a predetermined manner such as addition processing or reduction processing depending upon characteristics of the desired radiation image.

The radiation image storage panel 20 continuously advances in the direction indicated by the allow by means of the nip rolls 22*a*, 22*b*. Accordingly, the area of the storage panel which has been subjected to the stimulating step (i.e., reading step) is then subjected to an erasing step which uses an erasing lamp 30 such as a sodium lamp or a fluorescent lamp. In the erasing step, the radiation energy which still remains in the storage panel after being subjected to the reading step is almost completely released from the storage panel. Therefore, the radiation image storage panel having been subjected to the erasing step contains almost no latent image composed of the remaining radiation energy, and is favorably employed in the next cycle of the radiation image recording and reproducing method.

The stimulable phosphor sheet of the invention can be employed in a radiation image recording and reproducing method which comprises the steps of:

- recording a radiographic image on the stimulable phosphor sheet as a latent image,
- irradiating the latent image with stimulating rays transmitted through a guide to produce stimulated emission, under the condition that the stimulating rays are applied simultaneously in line in a direction traversing the stimulable phosphor sheet which moves in one direction relative to the position of the stimulating rays-transmitting guide,
- collecting the stimulated emission simultaneously on the line on which the stimulating rays are applied, and
- electrically processing the collected emission to reproduce the recorded radiographic image.

The above-described reading system (line-reading system) is further described with reference to FIGS. 12 to 15 of the attached drawings.

Figure 12:
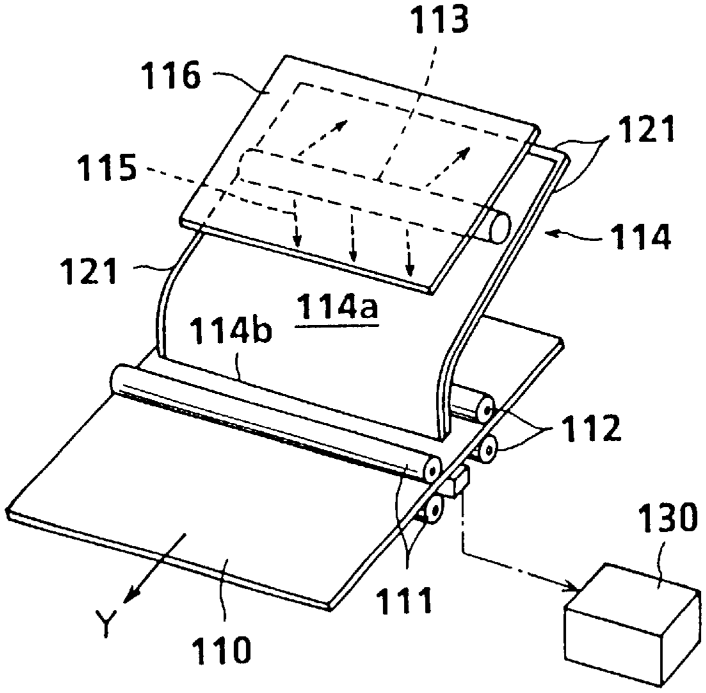
FIG. 12 is a schematic view illustrating a radiation image reproducing device which employs a line sensor.
Figure 13:
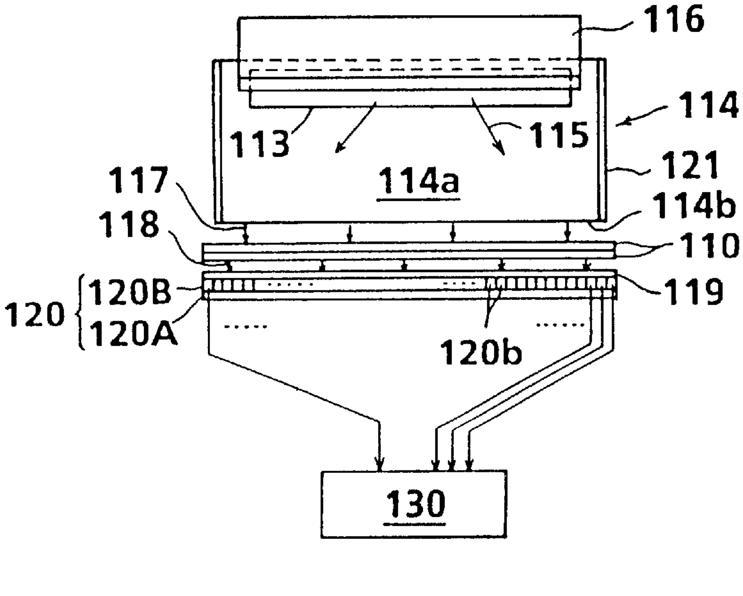
FIG. 13 is a schematic front view of the radiation image reproducing device of FIG. 12.
Figure 14:
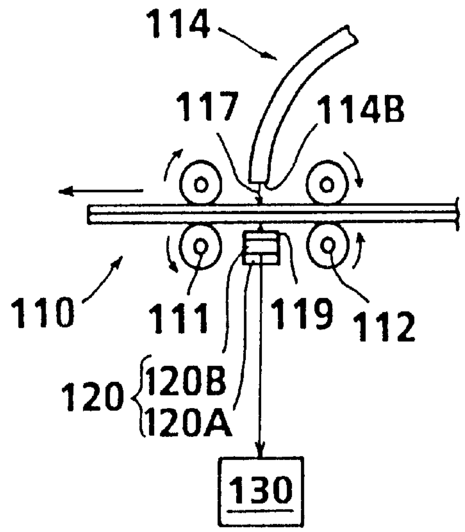
FIG. 14 is a schematic side view of the radiation image reproducing device of FIG. 12.

FIG. 12 is a schematic view of a radiation image line-reading system. FIG. 13 and FIG. 14 are a front section view and a side section view, respectively, of the reading system of FIG. 12.

In FIG. 12, a stimulable phosphor sheet 110 has a support on its lower side, and a protective film and a multi-layer filter (described hereinafter) on its upper side. In the stimulable phosphor sheet 110, a radiation image of a target object is recorded in the form of a latent image.

The stimulable phosphor sheet 110 is moved in the direction (Y) by means of two sets of nip rollers (transferring means) 111, 112. A fluorescent lamp 113 emits a light 115 of ultra-violet region. The ultra-violet light 115 is received and absorbed by a fluorescence-transmitting guide sheet 114 (which is placed under the fluorescent lamp 113) on its upper surface 114*a*. A portion of the ultra-violet light 115 advancing upward is reflected by a reflecting plate 116 and then received and absorbed by a fluorescence-transmitting guide sheet 114 on its upper surface 114*a*.

The fluorescence-transmitting guide sheet 114 is a plastic sheet-containing phosphor particles dispersed therein. The phosphor particles preferably absorb a ultra-violet light 115 emitted by a fluorescent lamp 113 and emit a fluorescent light (i.e., fluorescence) 117 having a main peak at a wavelength of 600 nm. Examples of the phosphor employable in this system include organic phosphor materials such as cumarin derivatives, thioxanthene derivatives, perylene derivatives, and polone derivatives. An example of the fluorescence-transmitting guide sheet is “LISA-PLASTIC” which is available from Bayer Japan, Ltd. The fluorescence-transmitting guide sheet 114 is coated with a light-reflecting material 121 such as vapor-deposited aluminum on three edge (or end) surfaces and is not coated on one end 114*b* positioned in the vicinity of the stimulable phosphor sheet 110. The ultra-violet light 115 received on the upper surface 114*a* excites phosphor particles in the guide sheet 114 to emit fluorescence 117. The fluorescence 117 is totally reflected repeatedly within the guide sheet 114 and finally comes out from the lower end 114*b* at high luminance. The light-reflecting material 121 may be a thin metal film or a white pigment layer. The fluorescence-transmitting guide sheet 114 may be further coated on its lower surface (opposite to the upper surface 114*a*) with a light-reflecting material 121.

The fluorescence 117 coming out from the lower end 114*b* of the fluorescence-transmitting guide sheet 114 is impinged onto the stimulable phosphor sheet 110 at an approximately right angle (i.e., incident angle is nearly 0°) so that the fluorescence is applied on the phosphor sheet 110 in line. The line of fluorescence 117 traverses the moving direction (Y) of the phosphor sheet 110. The fluorescence 117 has a wavelength peak corresponding to the stimulation region of the stimulable phosphor contained in the stimulable phosphor sheet 110. Accordingly, the stimulable phosphor particles incorporated in the area onto which the fluorescence 117 is applied produce an stimulated emission 118 in an amount proportional to the radiation energy stored in the area in the form of a latent image.

The fluorescence (stimulating rays) 117 impinged onto the stimulable phosphor sheet 110 at an incident angle of approximately 0° passes through the multi-layer filter at a transmittance of nearly 90% to reach the stimulable phosphor sheet 110 and stimulates the stimulable phosphor particles of the stimulable phosphor-incorporated area and the UV or visible light-emitting phosphor-containing partition in the phosphor sheet 110. Stimulating rays which are applied onto the phosphor sheet but are reflected on the phosphor sheet to return to the multi-layer filter are repeatedly reflected on the filter and finally reach onto the phosphor layer for stimulating the phosphor particles to produce the stimulated emission 118. Thus, the fluorescence (stimulating rays) 117 which is once enclosed within the space between the multi-layer filter and the stimulable phosphor sheet is finally utilized to stimulate the phosphor particles of the stimulable phosphor sheet 110. A portion of the stimulated emission 118 advancing upward is trapped with and reflected on the filter at almost 100% ratio independent of the incident angle and finally is collected by a line sensor 120 which is arranged under the phosphor sheet 110.

In the above-mentioned description, the stimulable phosphor sheet is moved, while the fluorescence-transmitting guide sheet is fixed. However, the guide sheet can be moved, while the stimulable phosphor sheet is fixed. The line of the stimulating rays applied onto the stimulable phosphor sheet can cover a line comprising a series of the stimulable phosphor-incorporated areas or a line of a plurality of series of the stimulable phosphor-incorporated areas aligned in parallel.

Figure 15:
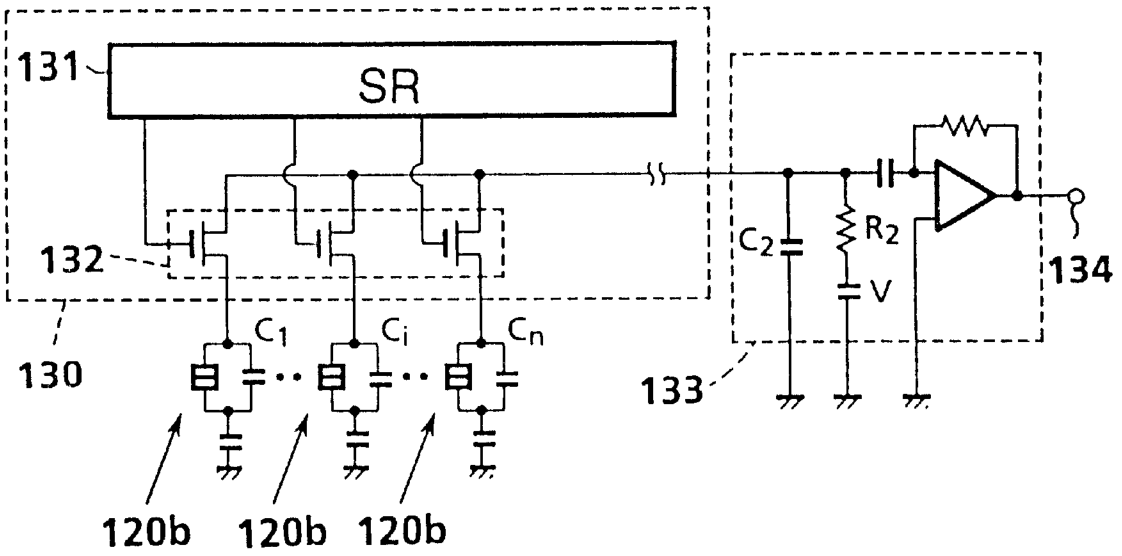
FIG. 15 is an electric circuit employed for operating the radiation image reproducing device of FIG. 12.

The stimulated emission 118 passes a selective filter 119 which absorbs the stimulating rays (fluorescence 117) and transmits only the stimulated emission to reach a line sensor 120. As illustrated in FIG. 14 and FIG. 15 in detail, the line sensor 120 comprises a support 120A extending on the width or traverse direction of the phosphor sheet 110 and a light-receiving array 120B which is divided into pixels and fixed onto the support 120A. The light-receiving array 120B is arranged in plural numbers in the width or traverse direction of the phosphor sheet. The array comprises a large number of solid photoelectric conversion elements 112*b* which correspond to respective pixels. The stimulated emission 118 is simultaneously received by the light-receiving elements arranged in series. The fluorescence (stimulating rays) 117 which passes the phosphor sheet 110 is absorbed by the selective filter 119 and therefore does not reach the solid photoelectric conversion elements 120*b*. The conversion elements 120*b* having received the stimulated emission produce photo-carriers and temporarily store the corresponding signals. The temporarily stored signals are sequentially read by a scanning circuit 130, and thus a series of linearly stimulated areas (which corresponds to a scanning line) is read to give signals corresponding to portion of radiation image.

The stimulable phosphor sheet 110 is then moved in the direction (Y) by the nip rollers 111, 112, in relation to the fluorescence-transmitting guide sheet 114 and the liner sensor 120 at a distance required for performing the next stimulating and reading procedure. These procedures are repeatedly performed on the whole surface of the stimulable phosphor sheet 110 to detect the whole radiation image stored in the phosphor sheet.

The scanning circuit 130 connected to the line sensor 120 is explained below.

FIG. 15 illustrates a line sensor utilizing a light-transmitting elements and an equivalent circuit of a scanning circuit. The signals given by photo-carriers which are produced in the solid photoelectric conversion element 120*b* utilizing the light-transmitting elements are stored and accumulated in the capacitors Ci (i=1, 2, - - - , n). The signals of the accumulated photo-carriers are sequentially read through on-off of a switching system 132 which is controlled by a shift register 131 in the scanning circuit 130, to give time-sequential image signals. The image signals are amplified in an amplifier 133 and are output at its output terminal 134. The image signals are utilized to display a radiation image on CRT or to produce a hard copy of the radiation image by means of a scan-recording devices. The MOS part comprising the shift register 131 and the switching system 132 can be replaced with CCD.

The stimulating light source composed of a fluorescent lamp 113 (which is used for stimulating in line the stimulable phosphor sheet 110) and the fluorescence-transmitting guide sheet 114 can be replaced with a simple system composed of a cold cathode fluorescent lamp (e.g., red fluorescent lamp) and a slit, or can be replaced with a system composed of a fluorescent lamp producing a ultra-violet rays and a combination of a fluorescence-transmitting guide sheet and an array of SELFOC lens (distributed index lens or gradient index lens). The fluorescent lamp can be replaced with a sodium lamp, a mercury lamp, or an electroluminescent panel.

The line-detecting means can be composed of an optical fiber (which converts the linear stimulated emission into planer stimulated emission) placed in the vicinity of the stimulable phosphor sheet and a combination of a filter, a lens and an area sensor, or can be composed of the optical fiber placed in the vicinity of the phosphor sheet and a combination of a filter, a SELFOC lens array and a line sensor, or can be composed of a SELFOC lens array, a filter (SELFOC lens array) and a line sensor.

The nip rollers 111, 112 for transferring the stimulable phosphor sheet 110 can be replaced with other means which can move the phosphor sheet, step by step, for conducting each scanning procedure without disturbing the arrangement of the source of stimulating rays and the light-detecting means.

The line sensor 120 can be placed on the same side (with respect to the stimulable phosphor sheet 110) on which the fluorescence-transmitting guide sheet 114. In this case, the stimulable phosphor sheet preferably has no multi-layer filter.

The stimulable phosphor sheet to be employed in the radiation image reproducing procedure preferably has, on a surface to be irradiated with the stimulating rays, a multi-layer filter having a reflectivity with respect to the stimulating rays which increase as an angle at which the stimulating rays are applied to the stimulable phosphor sheet increases and a reflectivity with respect to the stimulated emission which does not vary as an angle at which the stimulated emission comes out varies. The multi-layer filter comprises several or several tens thin layers (each layer having a thickness of an approximately ¼ λ) which are formed by alternately depositing under vacuum two or more materials having optical refractive index differing from each other, namely, a low refractive material and a high refractive material. The optical refractive index and the layer thickness are so selected as to give a variety of the desired characteristics. Examples of the low refractive materials include $SiO_2$ and $MgF_2$. Examples of the high refractive materials include $TiO_2$, $ZrO_2$ and ZnS. The multi-layer filter can be placed on the phosphor sheet in place of a protective film.

The multi-layer filter can be a band path filter which shows a transmittance of approximately 90% for a light of wavelength of 630–650 nm impinged at an incident angle 0° and almost no transmission for other light. The band path filter shows a transmittance decreasing when the light is impinged at incident angles other than 0°. For instance, the band bath filter shows a transmittance of approximately 0% when the light is impinged at an incident angle of 50°. Since the multi-layer filter absorb almost no light, the transmittance 0% means that almost 100% of light is reflected. Accordingly, stimulating rays applied at an incident angle of approximately 0° can be transmitted through the multi-layer filter at a transmittance of approximately 90% and reaches the stimulable phosphor sheet for stimulating the stimulable phosphor particles in the phosphor sheet. A portion of the stimulating rays which is diffused on the surface of the stimulable phosphor sheet and returns to the multi-layer filter is reflected on the surface of the filter at a high reflectivity and again addressed to the surface of the phosphor sheet. Almost 100% of the stimulated emission released from the stimulable phosphor sheet and advancing upward is reflected in the multi-layer filter and then directed to the lower side of the stimulable phosphor sheet. The provision of the multi-layer filter is effective for utilizing the stimulating rays efficiently and increasing the amount of the stimulated emission. Moreover, the provision of the multi-layer filter is effective for detecting the stimulated emission efficiently. More details of the multi-layer filter are described in Japanese Patent Provisional Publication 62-203465.

The examples embodying the invention and comparison examples are given below. In the examples and comparison examples, the reflectivity was measured by the following method.

[Measurement of Reflectivity]

The reflectivity (or reflectance) defined in the invention is measured by the following method.

A stimulable phosphor film, a stimulable phosphor sheet, a UV or visible light-emitting phosphor film, or an alumina film is sliced along its surface plane to give a thin film of 30 μm thick. The thin film is placed on a black support (showing a transmittance of less than 0.1% at a light of wavelength of 632.8 nm), and He-Ne laser beam (wavelength: 632.8 nm, corresponding to the second stimulation wavelength of BaFBr:Eu stimulable phosphor) having a beam diameter of 5 μm is applied onto the thin film at a right angle. The reflective light is detected by a 150 ϕ integrating sphere (150–0901) which is placed at an angle of 60° against the laser beam. The reflectivity is expressed in terms of percent unit (%) under the condition that the corresponding reflectivity measured on the standard white light reflection board is set to 100%.

COMPARISON EXAMPLE 1

A powder of stimulable BaFBr:Eu phosphor having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (1) having a thickness of approximately 250 μm.

COMPARISON EXAMPLE 2

A powder of stimulable BaFBr:Eu phosphor having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (2) having a thickness of approximately 215 μm.

COMPARISON EXAMPLE 3

A powder of stimulable BaFBr:Eu phosphor having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (3) having a thickness of approximately 150 μm.

COMPARISON EXAMPLE 4

1) A powder of stimulable BaFBr:Eu phosphor having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor film (1) having a thickness of approximately 100 μm.

2) A powder of alumina having a median diameter of 1 μm and a thermoplastic high-molecular weight acrylic resin were dispersed in an organic solvent in a weight ratio of 20:1 to give an alumina dispersion. The alumina dispersion was coated on a temporary support having a releasing surface and dried to give a dry film. The dry film was peeled off from the temporary support to give an alumina film having a thickness of approximately 30 μm.

3) Each of the stimulable phosphor film (1) and the alumina film was cut to give each 350 square pieces (40 mm×40 mm). The square pieces were placed alternately one on another to give a laminate of 700 layers. The laminate was heated at 100° C. under a pressure of approximately 1 kg/cm$^2$ for 1 hour to give a laminate block (1).

4) The laminate block (1) was repeatedly sliced along the plane on which the sides of the each layers appeared, using a wide microtome to give 200 stimulable phosphor films (2) having a thickness of 100 μm and a striped structure.

5) The 200 stimulable phosphor films (2) and the aforementioned alumina films (200 films) are placed alternately one on another to produce a laminate of 400 layers. The laminate was heated at 100° C. under a pressure of approximately 1 kg/cm$^2$ for 1 hour to give a laminate block (2).

6) The laminate block (2) was sliced along the plane on which the edge of the striped pattern appeared, using a wide microtome to give a stimulable phosphor sheet (4) having a thickness of 215 μm and a cross striped structure.

EXAMPLE 1

1) A powder of ultraviolet light-emitting phosphor ($YTaO_4$) having a median diameter of 1 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a UV light-emitting phosphor film (3) having a thickness of approximately 30 μm.

2) The procedures of 2) to 6) of Comparison Example 4 were repeated except for replacing the alumina film with the UV light-emitting phosphor film (3), to give a stimulable phosphor sheet (5) having a thickness of approximately 215 μm and a cross striped structure.

EXAMPLE 2

1) A powder of ultraviolet light-emitting phosphor ($GdF_3$) having a median diameter of 1 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a UV light-emitting phosphor film (4) having a thickness of approximately 30 μm.

2) The procedures of 2) to 6) of Comparison Example 4 were repeated except for replacing the alumina film with the UV light-emitting phosphor film (4), to give a stimulable phosphor sheet (6) having a thickness of approximately 215 μm and a cross striped structure.

[Structure and Reflectivity]

The structures and reflectivities of the alumina film, and the stimulable phosphor films and the UV light-emitting phosphor films employed for the preparation of the stimulable phosphor sheets are set forth in Table 1.

TABLE 1

| | Stimulable phosphor sheet (constitution) | Reflectivity |
|---|---|---|
| Com. Ex. 1 | Stimulable phosphor sheet (1) | 85.0% |
| Com. Ex. 2 | Stimulable phosphor sheet (2) | 85.0% |
| Com. Ex. 3 | Stimulable phosphor sheet (3) | 85.0% |

TABLE 1-continued

| | Stimulable phosphor sheet (constitution) | Reflectivity |
|---|---|---|
| Com. Ex. 4 | Stimulable phosphor sheet (4) | |
| | Stimulable phosphor film (1) | 85.0% |
| | Partition: Alumina film | 88.2% |
| Example 1 | Stimulable phosphor sheet (5) | |
| | Stimulable phosphor film (1) | 85.0% |
| | P: UV-emitting phosphor film (3) | 88.0% |
| Example 2 | Stimulable phosphor sheet (6) | |
| | Stimulable phosphor film (1) | 85.0% |
| | P: UV-emitting phosphor film (4) | 87.9% |

[Sharpness and Sensitivity of Stimulable Phosphor Sheet]

(1) Sharpness

The sample (stimulable phosphor sheet) was irradiated with X-rays (10 mR) produced at a tube voltage of 80 kVp through a MrF (modified transfer function) chart, and then stimulated with a He-Ne laser beam (wavelength: 632.8 nm). The stimulated emission emitted from the sample was collected by a photomultiplier (spectral sensitivity S-5). The collected emission was converted into electric signals which were then converted for reproducing the radiation image on a display device. The modified transfer function (MTF) of the reproduced radiation image was measured and expressed in terms of a spatial frequency (2 cycle/mm, namely 2 lp/mm). The spatial frequency of each stimulable phosphor sheet is set forth in Table 2.

(2) Sensitivity (PSL Sensitivity)

The sample (stimulable phosphor sheet) was irradiated with X-rays produced at a tube voltage of 80 kVp, and then stimulated with a He-Ne laser beam (wavelength: 632.8 nm). The amount of the stimulated emission emitted from the sample was measured and expressed in terms of a relative value for comparing the sensitivity. The amount of the stimulated emission expressed in terms of PSL sensitivity is set forth in Table 2.

TABLE 2

| | Stimulable phosphor sheet | Sharpness (MTF) | Sensitivity (PSL) |
|---|---|---|---|
| Comparison Examples | | | |
| 1 | Stimulable phosphor sheet (1) | 50 | 73 |
| 2 | Stimulable phosphor sheet (2) | 52 | 68 |
| 3 | Stimulable phosphor sheet (3) | 56 | 59 |
| 4 | Stimulable phosphor sheet (4) | 63 | 49 |
| Examples | | | |
| 1 | Stimulable phosphor sheet (5) | 63 | 51 |
| 2 | Stimulable phosphor sheet (6) | 63 | 52 |

Figure 16:
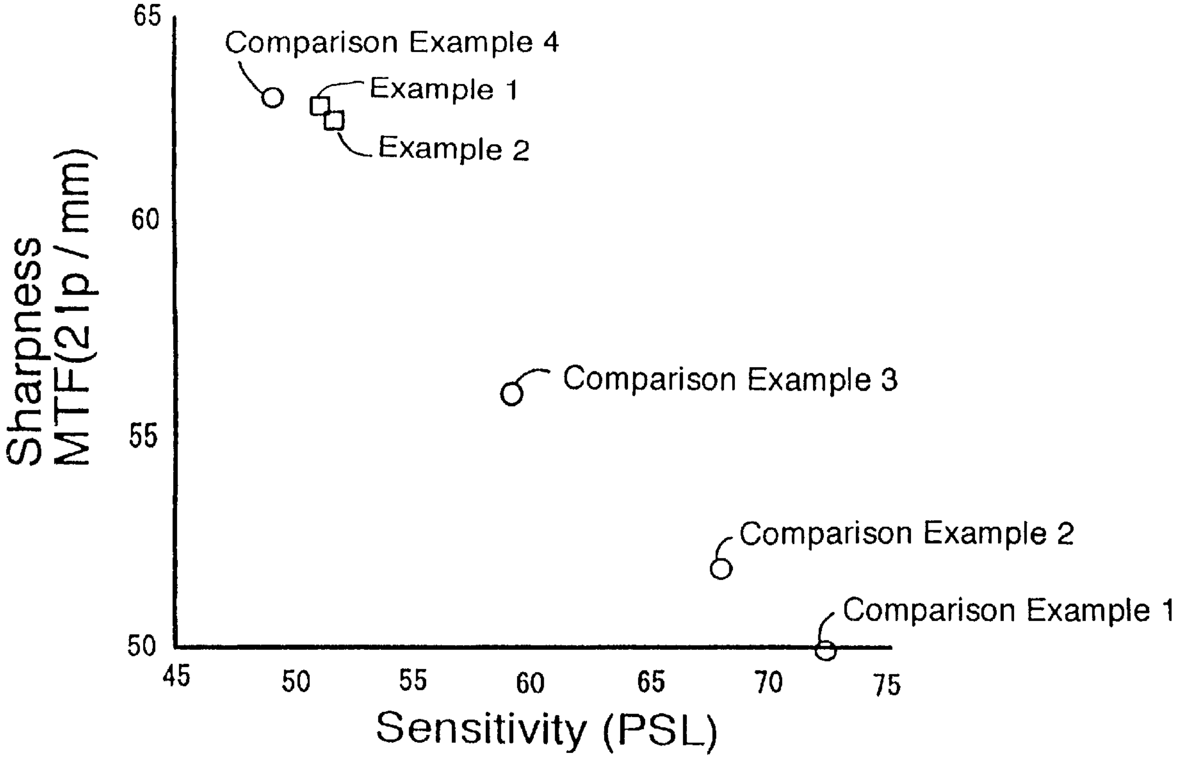
FIGS. 16 to 18 graphically illustrate the relationship between the sensitivity (of the stimulable phosphor sheet) and the sharpness (of reproduced radiation image) of stimulable phosphor sheets prepared in Examples embodying the invention and Comparison Examples.

The relationship between the sharpness (in terms of relative MTF value) and the sensitivity (in terms of PSL sensitivity) is graphically illustrated in FIG. 16. The graphical illustration clearly indicates that the stimulable phosphor sheets of Examples 1 to 2 (which embody the present invention) show a well balanced relationship between sharpness and sensitivity, as compared with the stimulable phosphor sheets of Comparison Examples 1 to 4.

COMPARISON EXAMPLE 5

A powder of stimulable phosphor ($YLuSiO_5$:Ce,Zr) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (7) having a thickness of approximately 250 μm.

COMPARISON EXAMPLE 6

A powder of stimulable phosphor ($YLuSiO_5$:Ce,Zr) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (8) having a thickness of approximately 215 μm.

COMPARISON EXAMPLE 7

A powder of stimulable phosphor ($YLuSiO_5$:Ce,Zr) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (9) having a thickness of approximately 150 μm.

COMPARISON EXAMPLE 8

1) A powder of stimulable phosphor ($YLuSiO_5$:Ce,Zr) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor film (5) having a thickness of approximately 100 μm.

2) A powder of alumina having a median diameter of 1 μm and a thermoplastic high-molecular weight acrylic resin were dispersed in an organic solvent in a weight ratio of 20:1 to give an alumina dispersion. The alumina dispersion was coated on a temporary support having a releasing surface and dried to give a dry film. The dry film was peeled off from the temporary support to give an alumina film having a thickness of approximately 30 μm.

3) Each of the stimulable phosphor film (5) and the alumina film was cut to give each 350 square pieces (40 mm×40 mm). The square pieces were placed alternately one on another to give a laminate of 700 layers. The laminate was heated at 100° C. under a pressure of approximately 1 $kg/cm^2$ for 1 hour to give a laminate block (3).

4) The laminate block (3) was repeatedly sliced along the plane on which the sides of the each layers appeared, using a wide microtome to give 200 stimulable phosphor films (6) having a thickness of 100 μm and a striped structure.

5) The 200 stimulable phosphor films (6) and the aforementioned alumina films (200 films) are placed alternately one on another to produce a laminate of 400 layers. The laminate was heated at 100° C. under a pressure of approximately 1 $kg/cm^2$ for 1 hour to give a laminate block (4).

6) The laminate block (4) was sliced along the plane on which the edge-of the striped pattern appeared, using a wide microtome to give a stimulable phosphor sheet (10) having a thickness of 215 μm and a cross striped structure.

EXAMPLE 3

1) A powder of ultraviolet light-emitting phosphor ($YTaO_4$) having a median diameter of 1 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a UV light-emitting phosphor film (7) having a thickness of approximately 30 μm.

2) The procedures of 2) to 6) of Comparison Example 8 were repeated except for replacing the alumina film with the UV light-emitting phosphor film (7), to give a stimulable phosphor sheet (11) having a thickness of approximately 215 μm and a cross striped structure.

EXAMPLE 4

1) A powder of ultraviolet light-emitting phosphor ($GdF_3$) having a median diameter of 1 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a UV light-emitting phosphor film (8) having a thickness of approximately 30 μm.

2) The procedures of 2) to 6) of Comparison Example 8 were repeated except for replacing the alumina film with the UV light-emitting phosphor film (8), to give a stimulable phosphor sheet (12) having a thickness of approximately 215 μm and a cross striped structure.

[Structure and Reflectivity]

The structures and reflectivities of the alumina film, and the stimulable phosphor films and the UV light-emitting phosphor films employed for the preparation of the stimulable phosphor sheets are set forth in Table 3.

TABLE 3

| | Stimulable phosphor sheet (constitution) | Reflectivity |
|---|---|---|
| Com. Ex. 5 | Stimulable phosphor sheet (7) | 84.0% |
| Com. Ex. 6 | Stimulable phosphor sheet (8) | 84.0% |
| Com. Ex. 7 | Stimulable phosphor sheet (9) | 84.0% |
| Com. Ex. 8 | Stimulable phosphor sheet (10) | |
| | Stimulable phosphor film (5) | 84.0% |
| | Partition: Alumina film | 88.2% |
| Example 3 | Stimulable phosphor sheet (11) | |
| | Stimulable phosphor film (5) | 84.0% |
| | P: UV-emitting phosphor film (7) | 87.2% |
| Example 4 | Stimulable phosphor sheet (12) | |
| | Stimulable phosphor film (5) | 84.0% |
| | P: UV-emitting phosphor film (8) | 87.3% |

[Sharpness and Sensitivity of Stimulable Phosphor Sheet]

The sharpness and the PSL sensitivity were measured and determined in the aforementioned manners. The amount of the stimulated emission expressed in terms of PSL sensitivity is set forth in Table 4.

TABLE 4

| | Stimulable phosphor sheet | Sharpness (MTF) | Sensitivity (PSL) |
|---|---|---|---|
| Comparison Examples | | | |
| 5 | Stimulable phosphor sheet (7) | 50 | 110 |
| 6 | Stimulable phosphor sheet (8) | 52 | 100 |
| 7 | Stimulable phosphor sheet (9) | 56 | 89 |
| 8 | Stimulable phosphor sheet (10) | 63 | 74 |
| Examples | | | |
| 3 | Stimulable phosphor sheet (11) | 63 | 77 |
| 4 | Stimulable phosphor sheet (12) | 63 | 75 |

Figure 17:
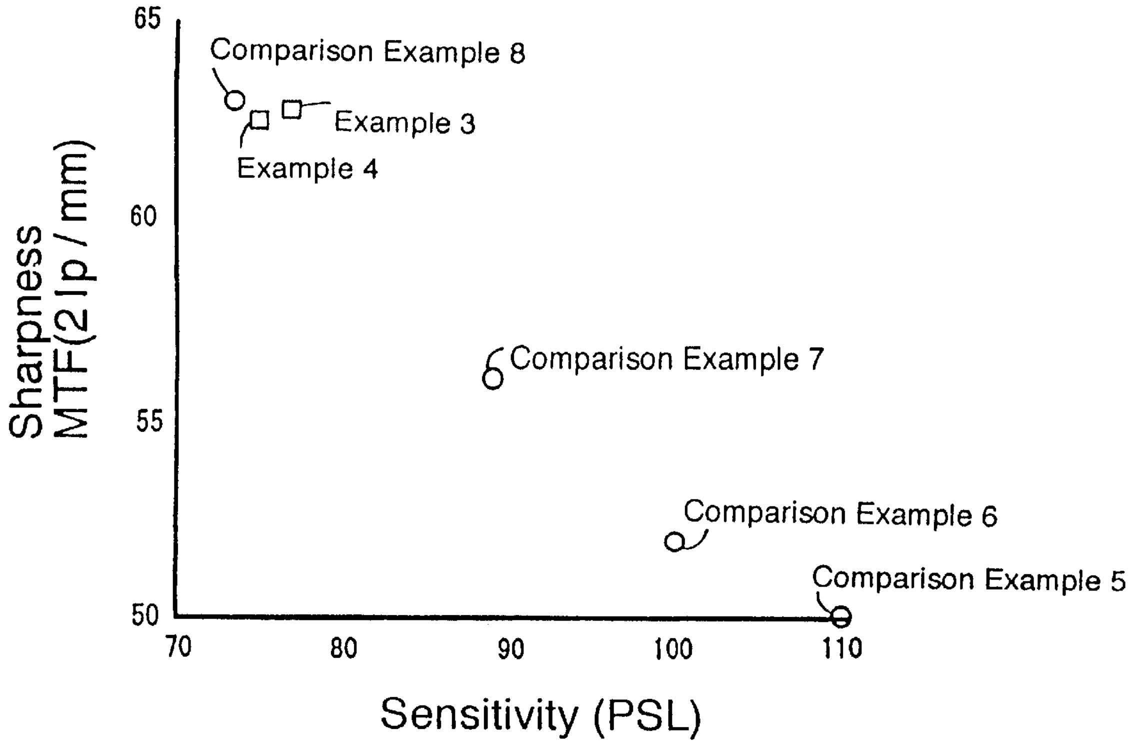

The relationship between the sharpness (in terms of relative MTF value) and the sensitivity (in terms of PSL sensitivity) is graphically illustrated in FIG. 17 The graphical illustration clearly indicates that the stimulable phosphor sheets of Examples 3 to 4 (which embody the present invention) show a well balanced relationship between sharpness and sensitivity, as compared with the stimulable phosphor sheets of Comparison Examples 5 to 8.

COMPARISON EXAMPLE 9

A powder of stimulable phosphor (SrS:Ce,Sm) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (13) having a thickness of approximately 250 μm.

COMPARISON EXAMPLE 10

A powder of stimulable phosphor (SrS:Ce,Sm) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (14) having a thickness of approximately 215 μm.

COMPARISON EXAMPLE 11

A powder of stimulable phosphor (SrS:Ce,Sm) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor sheet (15) having a thickness of approximately 150 μm.

COMPARISON EXAMPLE 12

1) A powder of stimulable phosphor (SrS:Ce,Sm) having a median diameter of 5 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a stimulable phosphor film (9) having a thickness of approximately 100 μm.

2) A powder of alumina having a median diameter of 1 μm and a thermoplastic high-molecular weight acrylic resin were dispersed in an organic solvent in a weight ratio of 20:1 to give an alumina dispersion. The alumina dispersion was coated on a temporary support having a releasing surface and dried to give a dry film. The dry film was peeled off from the temporary support to give an alumina film having a thickness of approximately 30 μm.

3) Each of the stimulable phosphor film (9) and the alumina film was cut to give each 350 square pieces (40 mm×40 mm). The square pieces were placed alternately one on another to give a laminate of 700 layers. The laminate was heated at 100° C. under a pressure of approximately 1 kg/cm$^2$ for 1 hour to give a laminate block (5).

4) The laminate block (5) was repeatedly sliced along the plane on which the sides of the each layers appeared, using a wide microtome to give 200 stimulable phosphor films (10) having a thickness of 100 μm and a striped structure.

5) The 200 stimulable phosphor films (10) and the aforementioned alumina films (200 films) are placed alternately one on another to produce a laminate of 400 layers. The laminate was heated at 100° C. under a pressure of approximately 1 kg/cm$^2$ for 1 hour to give a laminate block (6).

6) The laminate block (6) was sliced along the plane on which the edge of the striped pattern appeared, using a wide microtome to give a stimulable phosphor sheet (16) having a thickness of 215 μm and a cross striped structure.

EXAMPLE 5

1) A powder of ultraviolet light-emitting phosphor (BaFBr:Eu) having a median diameter of 1 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give UV light-emitting phosphor film (11) having a thickness of approximately 30 μm.

2) The procedures of 2) to 6) of Comparison Example 8 were repeated except for replacing the alumina film with the UV light-emitting phosphor film (11), to give a stimulable phosphor sheet (17) having a thickness of approximately 215 μm and a cross striped structure.

EXAMPLE 6

1) A powder of ultraviolet light-emitting phosphor (BaFBr:Eu) having a median diameter of 3 μm and a thermoplastic high-molecular weight polyester resin were dispersed in an organic solvent in a weight ratio of 20:1 to give a phosphor dispersion. The phosphor dispersion was coated on a temporary support having a releasing surface and dried to give a dry film. The dry film was peeled off from the temporary support to give a UV light-emitting phosphor film (12) having a thickness of approximately 30 μm.

2) The procedures of 2) to 6) of Comparison Example 12 were repeated except for replacing the alumina film with the UV light-emitting phosphor film (12), to give a stimulable phosphor sheet (18) having a thickness of approximately 215 μm and a cross striped structure.

[Structure and Reflectivity]

The structures and reflectivities of the alumina film, and the stimulable phosphor films and the UV light-emitting phosphor films employed for the preparation of the stimulable phosphor sheets are set forth in Table 5.

TABLE 5

| | Stimulable phosphor sheet (constitution) | Reflectivity |
|---|---|---|
| Com. Ex. 9 | Stimulable phosphor sheet (13) | 84.7% |
| Com. Ex. 10 | Stimulable phosphor sheet (14) | 84.7% |
| Com. Ex. 11 | Stimulable phosphor sheet (15) | 84.7% |
| Com. Ex. 12 | Stimulable phosphor sheet (16) | |
| | Stimulable phosphor film (9) | 84.7% |
| | Partition: Alumina film | 88.2% |
| Example 5 | Stimulable phosphor sheet (17) | |
| | Stimulable phosphor film (9) | 84.7% |
| | P: UV-emitting phosphor film (11) | 87.7% |
| Example 6 | Stimulable phosphor sheet (18) | |
| | Stimulable phosphor film (9) | 84.7% |
| | P: UV-emitting phosphor film (12) | 86.0% |

[Sharpness and Sensitivity of Stimulable Phosphor Sheet]

The sharpness and the PSL sensitivity were measured and determined in the aforementioned manners. The amount of the stimulated emission expressed in terms of PSL sensitivity is set forth in Table 6.

TABLE 6

| | Stimulable phosphor sheet | Sharpness (MTF) | Sensitivity (PSL) |
|---|---|---|---|
| Comparison Examples | | | |
| 9 | Stimulable phosphor sheet (13) | 50 | 110 |
| 10 | Stimulable phosphor sheet (14) | 52 | 100 |
| 11 | Stimulable phosphor sheet (15) | 56 | 89 |
| 12 | Stimulable phosphor sheet (16) | 63 | 74 |
| Examples | | | |
| 5 | Stimulable phosphor sheet (17) | 63 | 108 |
| 6 | Stimulable phosphor sheet (18) | 61 | 122 |

Figure 18:
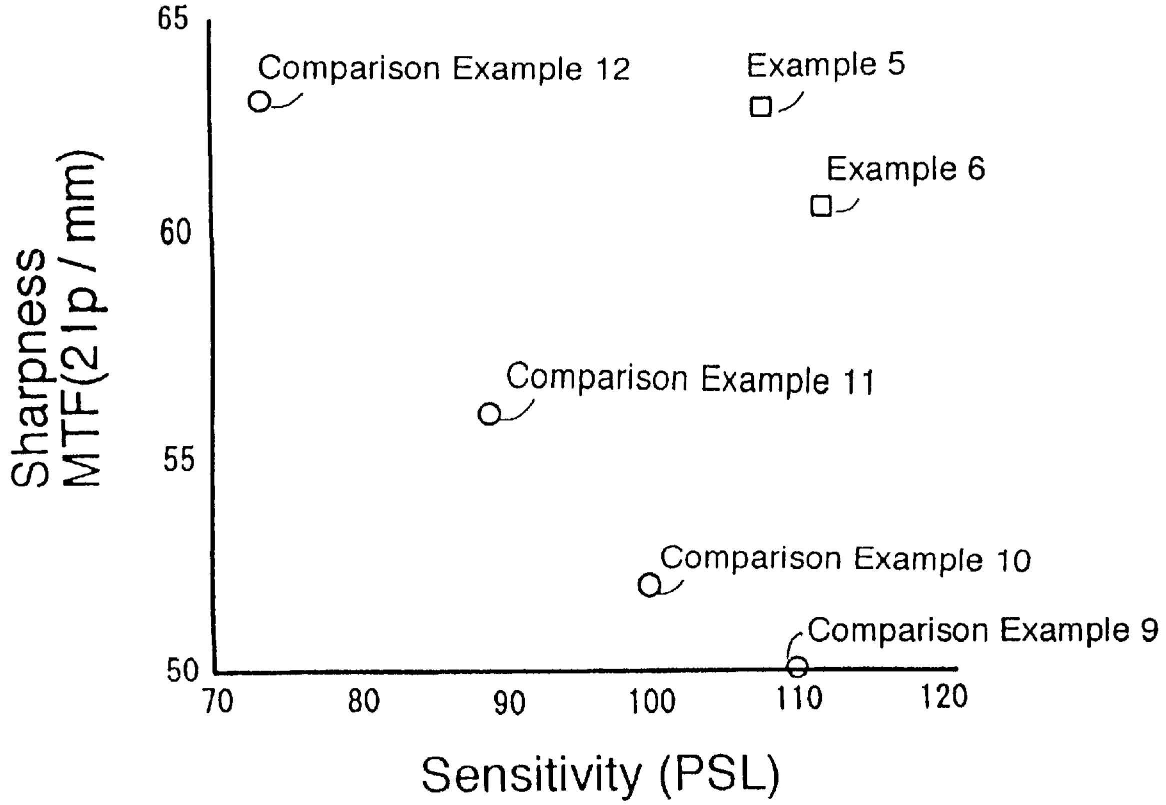

The relationship between the sharpness (in terms of relative MTF value) and the sensitivity (in terms of PSL sensitivity) is graphically illustrated in FIG. 18 The graphical illustration clearly indicates that the stimulable phosphor sheets of Examples 5 to 6 (which embody the present invention) show a well balanced relationship between sharpness and sensitivity, as compared with the stimulable phosphor sheets of Comparison Examples 9 to 12.

What is claimed is:

1. A stimulable phosphor sheet for a radiation image recording and reproducing method comprising the steps of recording as a latent image a radiographic image which is formed by application of radiation, irradiating the latent image with stimulating rays to release stimulated emission, and electrically processing the emission to reproduce the radiographic image, which comprises:

a partition containing a phosphor that emits a light in a ultraviolet or visible region upon absorbing the applied radiation, which divides the stimulable phosphor sheet on its plane into small sections, and a stimulable phosphor-incorporated area which is divided with the partition and which has a reflectivity with respect to the stimulating rays differing from a reflectivity with respect to the stimulating rays of the stimulable phosphor-containing partition.

2. The stimulable phosphor sheet of claim 1, wherein the reflectivity of the stimulable phosphor-incorporated area is higher than the reflectivity of the phosphor-containing partition.

3. The stimulable phosphor sheet of claim 1, wherein the reflectivity of the stimulable phosphor-incorporated area is lower than the reflectivity of the phosphor-containing partition.

4. The stimulable phosphor sheet of claim 1, which has a support on one side and a transparent protective film on another side.

5. The stimulable phosphor sheet of claim 1, wherein the phosphor-containing partition comprises phosphor particles that emit a light in a ultraviolet or visible region upon absorbing the applied radiation and a binder, and the stimulable phosphor-incorporated area comprises stimulable phosphor particles and a binder.

6. The stimulable phosphor sheet of claim 1, wherein the stimulable phosphor-incorporated area is divided and surrounded with the phosphor-containing partition.

7. The stimulable phosphor sheet of claim 1, wherein a stimulating ray-reflecting layer is provided on a surface opposite to a surface on which the stimulating rays impinge.

8. The stimulable phosphor sheet of claim 1, wherein a stimulated emission-reflecting layer is provided on a surface opposite to a surface on which the stimulating rays impinge.

9. The stimulable phosphor sheet of claim 1, wherein the phosphor-containing partition has a height in the range of 1/3 to 1/1 of the thickness of the stimulable phosphor sheet.

10. The stimulable phosphor sheet of claim 1, wherein the phosphor-containing partition contains white fine particles.

11. The stimulable phosphor sheet of claim 1, wherein the stimulable phosphor-incorporated area contains a dye absorbing the stimulating rays.

12. The stimulable phosphor sheet of claim 1, wherein the phosphor-containing partition further contains a dye absorbing the stimulating rays.

13. The stimulable phosphor sheet of claim 1, wherein the phosphor contained in the partition and the stimulable phosphor incorporated in the stimulable phosphor-incorporated area both are in the form of fine particles, and the phosphor in the partition has a mean particle size smaller than that of the stimulable phosphor in the stimulable phosphor-incorporated area.

14. The stimulable phosphor sheet of claim 1, wherein the phosphor contained in the partition and the stimulable phosphor incorporated in the stimulable phosphor-incorporated area both are in the form of fine particles, and the phosphor in the partition has a mean particle size larger than that of the stimulable phosphor in the stimulable phosphor-incorporated area.

15. The stimulable phosphor sheet of claim 1, wherein the phosphor-containing partition comprises phosphor particles that emit a light in a ultraviolet or visible region upon absorbing the applied radiation and a binder, and the stimulable phosphor-incorporated area comprises stimulable phosphor particles and a binder, and a weight ratio of the phosphor particles to the binder in the partition is larger than a weight ratio of the phosphor particles to the binder in the stimulable phosphor-incorporated area.

16. The stimulable phosphor sheet of claim 1, wherein the phosphor-containing partition comprises phosphor particles that emit a light in a ultraviolet or visible region upon absorbing the applied radiation and a binder, and the stimulable phosphor-incorporated area comprises stimulable phosphor particles and a binder, and a weight ratio of the phosphor particles to the binder in the partition is smaller than a weight ratio of the phosphor particles to the binder in the stimulable phosphor-incorporated area.

17. A radiation image recording and reproducing method which comprises the steps of:

recording a radiographic image on the stimulable phosphor sheet of claim 1 as a latent image, irradiating the latent image with stimulating rays to release stimulated emission, and electrically processing the stimulated emission to reproduce the recorded radiographic image.

18. A radiation image recording and reproducing method which comprises the steps of:

recording a radiographic image on the stimulable phosphor sheet of claim 1 as a latent image, irradiating the latent image with stimulating rays to release stimulated emission, collecting the stimulated emission from both surfaces of the stimulable phosphor sheet, and electrically processing the collected emissions to reproduce the recorded radiographic image.

19. A radiation image recording and reproducing method which comprises the steps of:

recording a radiographic image on the stimulable phosphor sheet of claim 1 as a latent image, irradiating the latent image with stimulating rays transmitted through a guide to release stimulated emission, under the condition that the stimulating rays are applied simultaneously in line in a direction traversing the stimulable phosphor sheet which moves in one direction relative to the position of the stimulating rays-transmitting guide, collecting the stimulated emission simultaneously on the line on which the stimulating rays are applied, and electrically processing the collected emission to reproduce the recorded radiographic image.

20. The radiation image recording and reproducing method of claim 19, in which the stimulable phosphor sheet has, on a surface to be irradiated with the stimulating rays, a multi-layer filter having a reflectivity with respect to the stimulating rays which increase as an angle at which the stimulating rays are applied to the stimulable phosphor sheet increases and a reflectivity with respect to the stimulated emission which does not vary as an angle at which the stimulated emission comes out varies.

21. The radiation image recording and reproducing method of claim 19, in which the stimulating rays comprises fluorescence and the guide is a sheet comprising phosphor particles and a polymer binder which receives a light on one end or on one surface and then emits fluorescence from another end for irradiating the stimulable phosphor sheet simultaneously in line.

22. The radiation image recording and reproducing method of claim 19, wherein the stimulated emission emitted in line is collected simultaneously by a line sensor comprising plural solid photoelectric conversion elements aligned in one direction.

* * * * *